(12) United States Patent
Simmons

(10) Patent No.: US 10,470,728 B2
(45) Date of Patent: Nov. 12, 2019

(54) ORBITAL ROTATION POSITIONING DEVICE FOR A C-ARM OF AN IMAGING SYSTEM

(71) Applicant: General Electric Company, Schenectady, NY (US)

(72) Inventor: John Matthew Simmons, Salt Lake City, UT (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 338 days.

(21) Appl. No.: 15/464,562

(22) Filed: Mar. 21, 2017

(65) Prior Publication Data

US 2018/0271461 A1   Sep. 27, 2018

(51) Int. Cl.
*A61B 6/00* (2006.01)
*A61B 6/03* (2006.01)

(52) U.S. Cl.
CPC .............. *A61B 6/4441* (2013.01); *A61B 6/44* (2013.01); *A61B 6/4405* (2013.01); *A61B 6/547* (2013.01)

(58) Field of Classification Search
CPC ....... A61B 6/44; A61B 6/4405; A61B 6/4441; A61B 6/547
See application file for complete search history.

(56) References Cited

U.S. PATENT DOCUMENTS

2012/0219121 A1   8/2012   Simmons et al.
2012/0314843 A1*  12/2012  Limmer .............. A61B 6/4441
                                              378/197

FOREIGN PATENT DOCUMENTS

CA          2311307 A1 *   6/1999   ............ A61B 6/105

* cited by examiner

*Primary Examiner* — Mark R Gaworecki
(74) *Attorney, Agent, or Firm* — Fletcher Yoder, P.C.

(57) ABSTRACT

An X-ray imaging system is provided. The X-ray imaging system includes an X-ray radiation source, an X-ray detector, and a C-arm having the X-ray radiation source disposed on a first end and the X-ray detector disposed on a second end opposite the first end. The C-arm includes a track. The X-ray imaging system also includes a C-arm rotation device configured to enable the C-arm to rotate along the track in an orbital direction relative to the C-arm rotation device, wherein a portion of the C-arm rotation device is disposed within the track. The X-ray imaging system also includes an orbital rotation positioning device configured to be disposed within the track, wherein the orbital rotation positioning device blocks rotation of the C-arm beyond a position of the orbital rotation positioning device.

20 Claims, 9 Drawing Sheets

ORBITAL ROTATION POSITIONING DEVICE FOR A C-ARM OF AN IMAGING SYSTEM

BACKGROUND

The subject matter disclosed herein relates to X-ray imaging systems having C-arms and, more particularly, to orbital rotation positioning devices for the C-arms.

Medical diagnostic imaging systems generate images of an object, such as a patient, for example, through exposure to an energy source, such as X-rays passing through a patient, for example. The generated images may be used for many purposes. Often, when a practitioner takes X-rays of a patient, it is desirable to take several X-rays of one or more portions of the patient's body from a number of different positions and angles, and preferably without needing to frequently reposition the patient. To meet this need, C-arm X-ray diagnostic equipment has been developed. The term C-arm generally refers to an X-ray imaging device having a rigid and/or articulating structural member having an X-ray source and an image detector assembly that are each located at an opposing end of the structural member so that the X-ray source and the image detector face each other. The structural member is typically "C" shaped and so is referred to as a C-arm. In this manner, X-rays emitted from the X-ray source can impinge on the image detector and provide an X-ray image of the object or objects that are placed between the X-ray source and the image detector.

In many cases, C-arms are connected to one end of a movable arm. In such cases, the C-arm can often be raised and lowered, be moved from side to side, and/or be rotated about one or more axes of rotation. Accordingly, such C-arms can be moved and reoriented to allow X-ray images to be taken from several different positions and angles and different portions of a patient, without requiring the patient to be frequently repositioned. For example, the C-arm may be rotated in an orbital direction to a desired position (e.g., orbital angular position). However, if it desired to return to this position later, the position may need to be remembered (e.g., using a scale on the C-arm) or temporarily marked on the C-arm. To return to the desired position involves careful hand/eye coordination to ensure accuracy, which may be slow, tedious, and unreliable.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In a first embodiment, an X-ray imaging system is provided. The X-ray imaging system includes an X-ray radiation source, an X-ray detector, and a C-arm having the X-ray radiation source disposed on a first end and the X-ray detector disposed on a second end opposite the first end. The C-arm includes a track. The X-ray imaging system also includes a C-arm rotation device configured to enable the C-arm to rotate along the track in an orbital direction relative to the C-arm rotation device, wherein a portion of the C-arm rotation device is disposed within the track. The X-ray imaging system also includes an orbital rotation positioning device configured to be disposed within the track, wherein the orbital rotation positioning device blocks rotation of the C-arm beyond a position of the orbital rotation positioning device.

In a second embodiment, an orbital rotation positioning device is provided. The orbital rotation positioning device includes a first body portion having a first end configured to interface with a first surface of a track of a C-arm of an X-ray imaging system. The orbital rotation positioning device also includes a second body portion having a second end configured to interface with a second surface of the track opposite the first surface of the C-arm of the X-ray imaging system, wherein the first body portion is moveable relative to the second body portion. The orbital rotation positioning device is configured to be disposed within the track of the C-arm to block rotation of the C-arm beyond a position of the orbital rotation positioning device, and wherein the orbital rotation positioning device is configured to interchange between a first configuration and a second configuration, the first configuration is configured to lock the position of the orbital rotation positioning device within the track so that the orbital rotation positioning device does not move relative to the track, and the second configuration is configured to enable the position of the orbital rotation positioning device to be moved along the track.

In a third embodiment, an orbital rotation positioning device is provided. The orbital rotation positioning device includes a first body portion having a first end including a first end structure having a first end surface disposed on the end structure, and the first end surface is configured to interface with a first surface of a track of a C-arm of an X-ray imaging system. The orbital rotation positioning device also includes a second body portion having a second end comprising a second end structure having a second end surface, and the second end surface is configured to interface with a second surface of the track opposite the first surface of the C-arm of the X-ray imaging system, wherein the first body portion is moveable relative to the second body portion. The orbital rotation positioning device is configured to be disposed within the track of the C-arm to block rotation of the C-arm beyond a position of the orbital rotation positioning device, and wherein the orbital rotation positioning device is configured to interchange between a first configuration and a second configuration, the first configuration is configured to lock the position of the orbital rotation positioning device within the track so that the orbital rotation positioning device does not move relative to the track by having the first end surface and the second end surface respectively grip the first and second surfaces of the track, and the second configuration is configured to enable the position of the orbital rotation positioning device to be moved along the track by having respective portions of the first and second end structures extend away from the first and second end structures to contact the first and second surfaces, respectively, to keep the first and second end surfaces from gripping the first and second surfaces, respectively.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The following embodiments describe a device (e.g., orbital rotation positioning device) to enable a position (e.g., orbital angular position) of a C-arm of an X-ray imaging system to be set and returned to quickly and easily. In particular, the device is configured to be disposed within the track and to be set into different configurations. In a first configuration (e.g., locked configuration), the device can be locked into a position along the track (i.e., does not move relative to the track) to block rotation (e.g., in the orbital direction) of the C-arm beyond the position of the device. In a second configuration (e.g., unlocked configuration), the device can be unlocked to enable it to be slid along the track to a different position and/or to be removed from the track. The device provides a number of advantages over past techniques to mark the orbital angular position of the C-arm. In particular, the device is easy to use, intuitive, inexpensive, robust, and adjustable.

Figure 1:
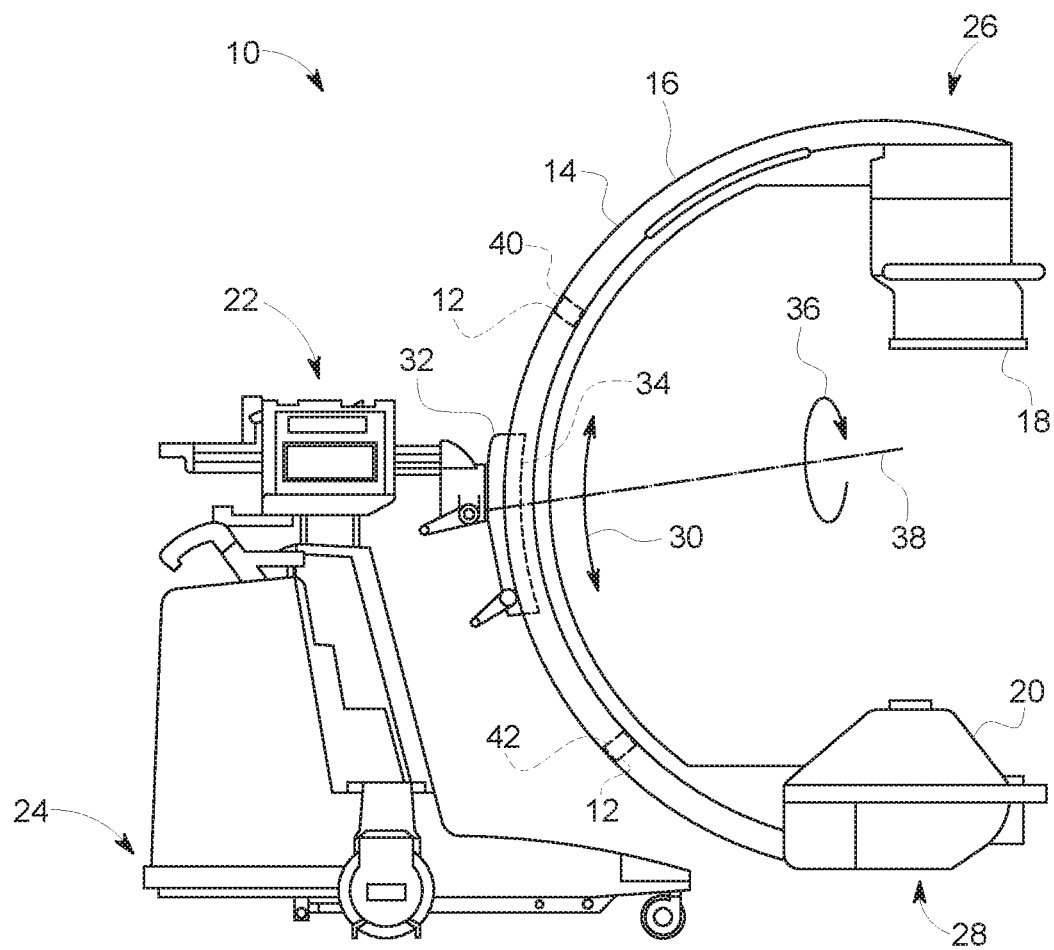
FIG. 1 is a side view of an embodiment of an X-ray imaging system (e.g., a mobile C-arm imaging system) having orbital rotation positioning devices disposed within a track of a C-arm.

FIG. 1 is a side view of an embodiment of an X-ray imaging system 10 (e.g., a mobile C-arm imaging system) having orbital rotation positioning devices 12 disposed within a track 14 of a C-arm 16. Although a mobile imaging system is illustrated, the embodiments described below may be utilized with any X-ray imaging system having a C-arm (e.g., a fixed imaging system). The system 10 includes a C-arm 16, an image receptor 18 (e.g., X-ray detector), an X-ray source 20, a support structure 22, and a wheeled base 24. The image receptor 18 and the X-ray source 20 are mounted at opposing locations (e.g., ends 26, 28) on the C-arm 16. The support structure 22 provides support for the C-arm 16 and holds the C-arm 16 in a suspended position. The support structure 22 is mounted on the wheeled base 24 that enables the system 10 to be moved.

The support structure 22 provides stable, balanced support for the C-arm 16. The support structure 22 suspends the C-arm 16 for use in imaging a patient or an object, for example. The support structure 22 also allows the C-arm 16 to be rotated about an axis of rotation (manually or using a motor, for example). For example, the C-arm 16 may be rotated in an orbital direction 30. As depicted, the support structure 22 includes a C-arm rotation device 32 (e.g., carriage) that enables the C-arm 16 to move or rotate in the orbital direction 30 along its track 14 relative to device 32. A portion 34 of the C-arm rotation device 32 is disposed within the track 14 to enable the C-arm 16 to move or rotate in the orbital direction 30. In certain embodiments, the C-arm rotation device 32 enables the C-arm to rotate or flip-flop (e.g., as indicated by reference numeral 36) about an axis 38 emanating from where the C-arm rotation device 32 is coupled to the C-arm 16. The support structure 22 is attached to the wheeled base 24, for example, to reposition the mobile C-arm imaging system 10.

The C-arm 16 allows the image receptor 18 and the X-ray source 20 to be mounted and positioned about an object to be imaged, such as a patient. The C-arm 16 may be a circular C-shaped or an arc-shaped member, for example. The C-arm 16 enables selective positioning of the image receptor 18 and the X-ray source 20 with respect to the width and length of the patient or other object located within the interior free space of the C-arm 16.

The image receptor 18 may be an image intensifier or other energy receptor for using in diagnostic imaging, for example. The image receptor 18 and the X-ray source 20 are mounted at opposing positions (e.g., ends 26, 28) on the C-arm 16. The image receptor 18 and the X-ray source 20 may be positioned about an object, such as a patient, using the C-arm 16 and support structure 22. The image receptor 18 and the X-ray source 20 are used to generate a diagnostic image representative of the object being imaged.

In operation, a patient, for example, is placed on a table that is positioned between the image receptor 18 and the X-ray source 20 mounted on the C-arm 16. The support structure 22 moves the C-arm 16. Moving the C-arm 16 positions the image receptor 18 and the X-ray source 20 at desired locations with respect to the patient. The image receptor 18 may be positioned near the patient in order to improve resulting image quality.

To mark a position (e.g., orbital angular position) for acquiring an image with the imaging system 10, one or more position marking devices 12 (e.g., orbital rotation positioning devices) may be disposed within the track 14. As depicted, a first orbital rotation positioning device 40 marks a first orbital angular position, while a second orbital positioning device 42 marks a second orbital angular position different from the first orbital angular position. The orbital rotation positioning devices 12 extend across an entire width of the track 14 to block movement of the C-arm 16 beyond a position of the respective device 12. In particular, the respective orbital rotation positioning device 12 blocks movement of the C-arm 16 upon the portion 34 of the C-arm 16 contacting the device 12. As described in greater detail below, the orbital rotation positioning device is interchangeable between two different configurations. In a first configuration (e.g., locked configuration), the device 12 can be locked into a position along the track 14 (i.e., does not move relative to the track 14) to block rotation (e.g., in the orbital direction 30) of the C-arm 16 beyond the position of the device 12. In a second configuration (e.g., unlocked configuration), the device 12 can be unlocked to enable it to be slid along the track 14 to a different position and/or to be removed from the track 14. The device 12 may be stored in an end of the track 14.

Figure 2:
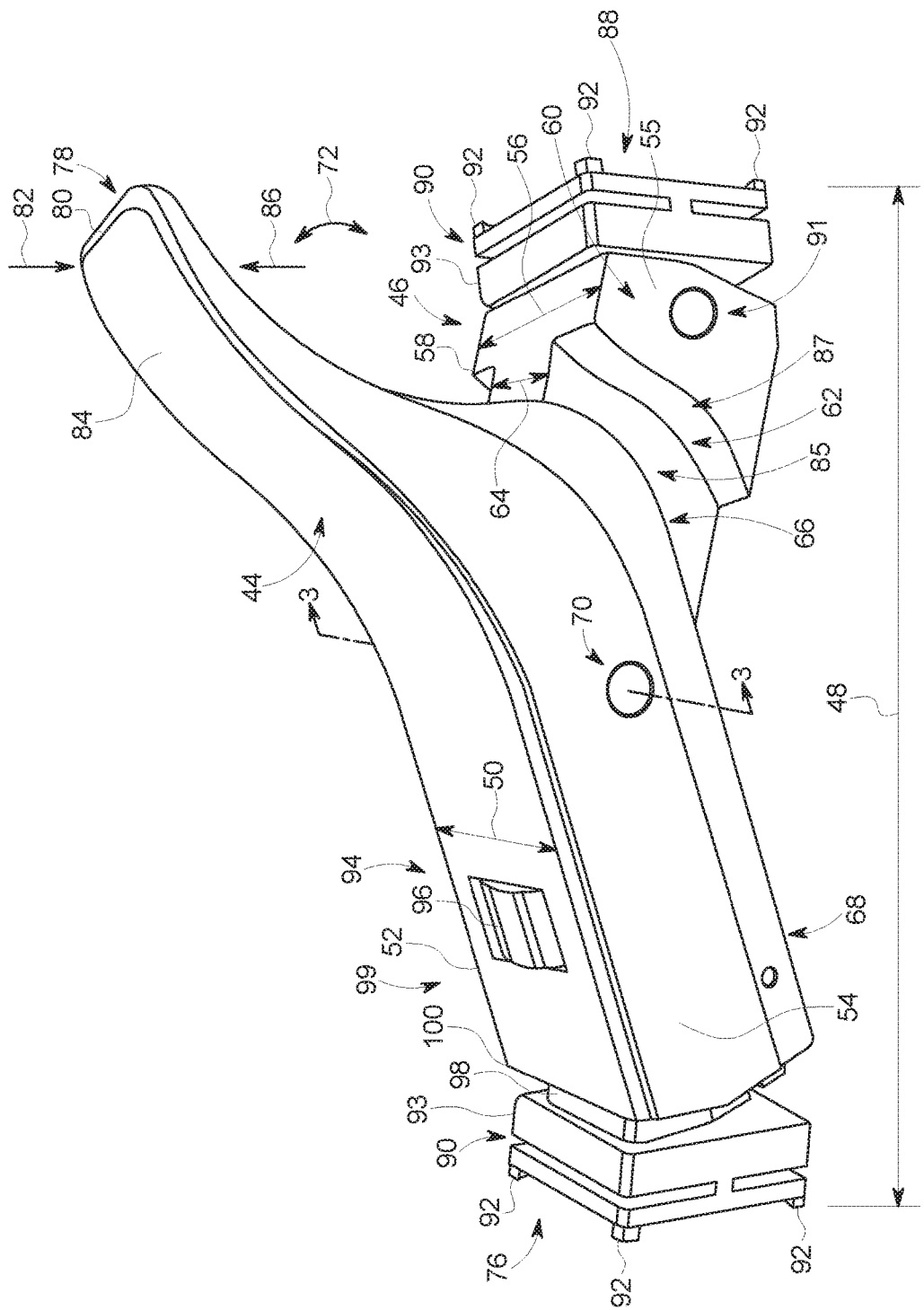
FIG. 2 is a side perspective view of an embodiment of an orbital rotation positioning device.

FIG. 2 is a side perspective view of an embodiment of the orbital rotation positioning device 12. The device 12 includes a first body portion 44 coupled to a second body portion 46. As depicted, the first body portion 44 is axially longer than the second body portion 46 along a longitudinal length 48 of the device 12. The first body portion 44 includes a width 50 (e.g., perpendicular to the longitudinal length 48) between sides 52, 54 of the first body portion 44. The second body portion 46 includes a first portion 55 having a width 56 between sides 58, 60 (e.g., perpendicular to the longitudinal length 48) of the second body portion 46. The width 56 may be the same or substantially the same (e.g., ±approximately 5 to 10 percent) as the width 50. The second body portion 46 includes a second portion 62 having a width 64 between the sides 58, 60. The width 56 is less than the width 64. In certain embodiments, the width 56 ranges from approximately 20 to 50 percent, 20 to 35 percent, or 35 to 50 percent, and all subranges therebetween less than the width 64. For example, the width 56 may be approximately 20, 25, 30, 35, 40, 45, or 50 percent less than the width 64.

Figure 3:
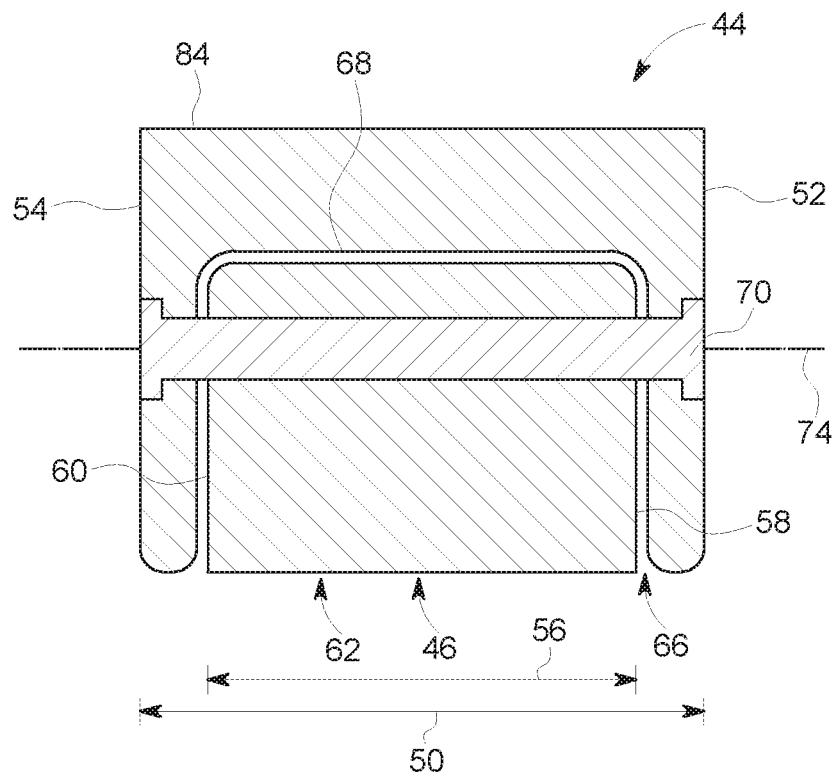
FIG. 3 is a cross-sectional view of an embodiment of the orbital rotation positioning device of FIG. 2 taken along line 3-3.

The second portion 62 of the second body portion 46 fits within a recess 66 formed within an underside 68 of the first body portion 44 extending between the sides 52, 54 (see FIG. 3). The second portion 62 is coupled to the first body portion 44 within the recess 66 via a fastener 70 (e.g., pin, rivet, etc.) extending through the sides 52, 54 of the first body portion 44 and the sides 58, 60 of the second portion 62. The fastener 70 enables rotational movement (as indicated by reference numeral 72) about an axis 74 (e.g., of the fastener 70) perpendicular to the longitudinal length 48 of the device 12 by forming a rotational joint.

The first body portion 44 includes ends 76, 78 (e.g., axial ends) disposed opposite each other. End 78 is adjacent the second body portion 46. A handle 80 extends (e.g., both axially and radially relative to the longitudinal length 48) from the end 78. As depicted, the handle 80 may be arcuate-shaped. The handle 80 extends over the second body portion 46. A force 82 applied to a top side 84 (e.g., extending between the sides 52, 54) of the handle 80 causes rotation 72 (e.g., about the rotational joint) of the first body portion 44 adjacent the second body portion 46 towards the second body portion 46 to put the device 12 in a locked configuration when disposed within the track 14 of the C-arm 16. The locked configuration keeps the device 12 from moving relative to the track 14. In the locked configuration, an arcuate-shaped portion 85 on the underside 86 of the first body portion 44 fits into a corresponding arcuate-shaped portion 87 of the second body portion 46 on both sides 58, 60. A force 86 applied to the underside 68 of the handle 80 causes rotation 72 (e.g., about the rotational joint) of the first body portion 44 adjacent the second body portion 46 away from the second body portion 46 to release the device from the locked configuration to an unlocked configuration. The unlocked configuration enables the device to be moved along the track 14 of the C-arm 16 or to be removed from the track 14 (e.g., via rotating the device 12). The longitudinal length 48 of the device 12 is greater in the locked configuration than the unlocked configuration.

The second body portion 46 includes an end (e.g., axial end) adjacent where the second body portion 46 is coupled to the first body portion 44 via the fastener 70 and an end 88 (e.g., axial end) disposed opposite the end adjacent the fastener 70. End 88 is opposite the end 76 of the first body portion 44. Ends 76, 88 are the axial ends of the device 12. Each end 76, 88 is configured to interface with a respective surface (e.g., inner surface) of the track 14. In particular, each end 76, 88 includes an end structure 90 (e.g., foot or claw-like structure). The end structure 90 may be made of plastic, polypropylene, glass filler, aluminum, or a combination thereof. The end structure 90 may include a surface (e.g., surface 110 in FIG. 4) that interfaces (e.g., contacts and/or grips) with the surface of the track 14. In certain embodiments, a pad may be disposed on the end structure 90 (e.g., on surface 110 in FIG. 4) that interfaces (e.g., contacts and/or grips) with the surface of the track 14. In certain embodiments, the pad may be made of polyurethane. A fastener 91 (e.g., pin, rivet, etc.) couples the end structure 90 of end 88 to the first portion 55 of the second body portion 46.

As depicted, portions 92 (e.g., feet or protrusions) extend away from the end 76, 88 and a main body portion 93 of the end structure 90. In the unlocked configuration, the portions 92 extend sufficiently away from the end 76, 88 and the end structure 90 to keep the surface of the end structure 90 or the pad between the portions 92 (at both ends 76, 88) from either contacting and/or sufficiently gripping the surface of the track 14 to enable the device 12 to be slid along the track 14. In certain embodiments, the pad or the surface of the end structure 90 is inset (e.g., axially relative to the longitudinal length 48) from the portions 92. In the locked configuration, the surface of the end structure 90 or the pad between the portions 92 (at both ends 76, 88) contacts and sufficiently grips the surface of the track 14 (e.g., creates sufficient friction) to block movement of the device 12 along the track 14.

In certain embodiments, the portions 92 may be retractable. For example, the portions 92 may include a mechanism (e.g., weak spring) that enable the portions 92 to retract towards the surface of the end structure 90 in the presence of sufficient force on the portions 92 (e.g., in the locked configuration) to enable the surface of the end structure 90 or the pad to contact the surface of the track 14. In the absence of sufficient force on the portions 92 (e.g., in the unlocked configuration), the portions 92 extend away from the surface of the end structure 90 to keep the surface of the end structure 90 or the pad from sufficiently contacting and gripping the surface of the track 14 (e.g., to generate enough friction) to block movement of the device 12. In certain embodiments, the retractable portions 92 may include protrusions, feet, ball springs, spring plungers, or another weak spring loaded device.

In certain embodiments, the surface of the end structure 90 may include a plurality of ridges. In the locked configuration, a sufficient number of ridges on the surface of the end structure 90 may contact and grip the surface of the track 14 to create enough friction to block movement of the device 12 along the track 14. In the unlocked configuration, only a few ridges on the surface of the end structure 90 may contact the surface of the track 12, thus, not creating enough friction to block movement of the device 12.

In certain embodiments, the longitudinal length 48 of the device 12 is adjustable via a length adjusting mechanism 94. The length adjusting mechanism 94 is disposed within the first body portion 44 (e.g., adjacent the end 76). In certain embodiments, the length adjusting mechanism 94 may include a nut and screw assembly. As depicted, the length adjusting mechanism 94 includes a knob or thumb wheel 96 (e.g., nut) coupled to a screw (not shown) disposed within the first body portion 44. The screw is coupled to a telescoping portion or extension 98 disposed between the end structure 90 and an end 100 of the main portion 99 of the first body portion 44. The extension 98 is partially disposed within the main portion 99 of the first body portion 44. Also, the extension 98 couples the end structure 90 to the main portion 99 of the first body portion 44. Rotation of the knob 96 (e.g., circumferentially relative to the longitudinal length 48) in a first circumferential direction causes the extension 98 (and thus the end 76) to extend away (e.g., axially relative to the longitudinal length 48) from the main portion 99 of the first body portion 44 to lengthen the longitudinal length 48 of the device 12. Rotation of the knob in a second circumferential direction (opposite the first circumferential direction) causes the extension 98 (and thus the end 76) to retract (e.g., axially relative to the longitudinal length 48) towards the main portion 99 of the first body portion 44 to shorten the longitudinal length 48 of the device 12.

In certain embodiments, the main portion 99 of the first body portion 44 and the first and second portions 55, 62 of the second body portion 46 may be manufactured via additive manufacturing, injection molding, or another technique. In certain embodiments, the portions 55, 62, 99 may be made of plastic.

Figure 4:
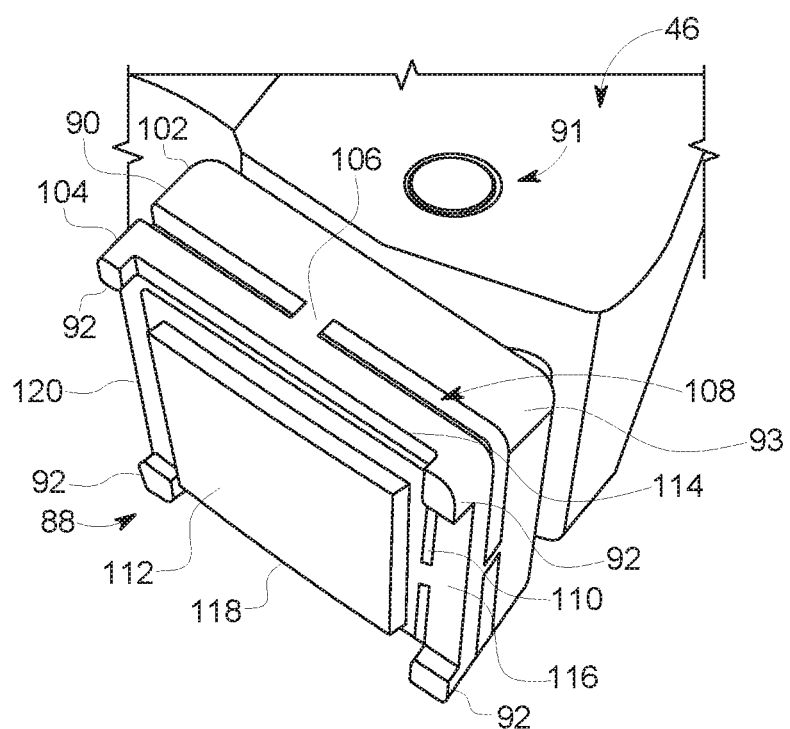
FIG. 4 is a perspective view of an embodiment of an end of the orbital rotation positioning device of FIG. 2.

FIG. 4 is a perspective view of an end (e.g., ends 76, 88) of the orbital rotation positioning device 12 of FIG. 2. As depicted, the end 78 is of the second body portion 46 of the device 12. The description of the end 88 also applies to the end 76. The end structure 90 is coupled to the second body portion 46 via the fastener 91 as described above. As depicted, the end structure 90 includes a first layer 102 coupled to a second layer 104 via spacers or columns 106 disposed between the first and second layers 102, 104. The spacers 106 create a gap 108 between the first and second layers 102, 104. In certain embodiments, the end structure 90 may include a single layer. In certain embodiments, the end structure 90 may include a different configuration. The end structure 90 may be made of plastic, polypropylene, glass filler, aluminum, or a combination thereof. The end structure 90 includes a surface 110 that faces the surface of the track 14. As depicted, a pad 112 (e.g., rubber pad) is disposed on the end structure 90. In the locked configuration, the pad 112 contacts and grips the surface of the track 14 to generate enough friction to block movement of the device 12. In the unlocked configuration, the pad 112 does not contact or minimally contacts the surface of the track 14 to reduce or avoid friction to enable movement (e.g., sliding) of the device 12 along the track 14. In certain embodiments, no pad may be coupled to the surface 110. Instead, the surface 110 may directly face and interface with the surface of the track 14.

As depicted, portions 92 (e.g., feet or protrusions) extend away from the end 88 and the end structure 90. As depicted, 2 portions 92 are disposed on each edge 114, 116, 118, 120 of the end structure 90 (e.g., second layer 104). In other embodiments, the number of portions 92 on each edge 114, 116, 118, 120 may vary (e.g., from 1 to 4 or more). In the unlocked configuration, the portions 92 extend sufficiently away from the end 76, 88 and the end structure 90 to keep the pad 112 between the portions 92 from either contacting and/or sufficiently gripping the surface of the track 14 to enable the device 12 to be slid along the track 14. In the locked configuration, the second layer 104 near the portion 92 is pushed (e.g., axially) towards the first layer 102 (e.g., reducing the gap 108) to enable the pad 112 between the portions 92 to contact and sufficiently grip the surface of the track 14 (e.g., creates sufficient friction) to block movement of the device 12 along the track 14.

Figure 5:
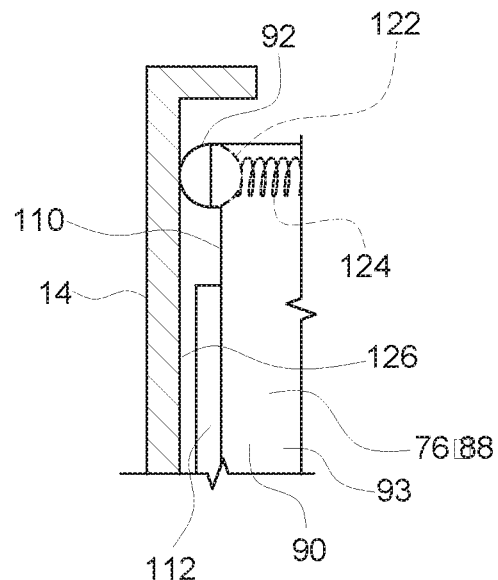
FIG. 5 is a partial view of an embodiment of a portion of an end of the orbital rotation positioning device (e.g., in an unlocked configuration) of FIG. 2 interfacing with a track of a C-arm.
Figure 6:
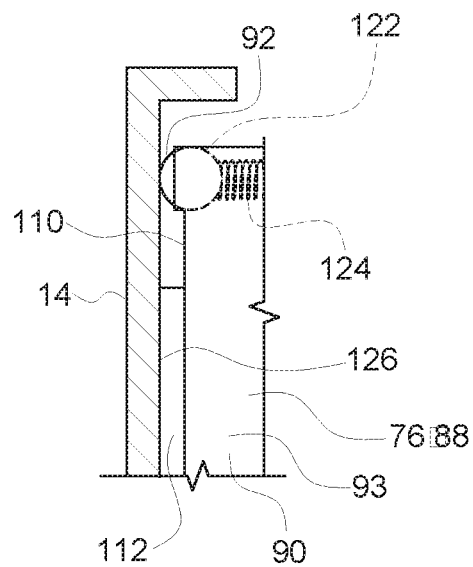
FIG. 6 is a partial view of an embodiment of a portion of an end of the orbital rotation positioning device (e.g., in the locked configuration) of FIG. 2 interfacing with a track of a C-arm.

As mentioned above, the portions 92 may be retractable 92. FIGS. 5 and 6 are partial views of a portion of an end (e.g., end 76, 88) of the orbital rotation positioning device 12 of FIG. 2 interfacing with the track 14 of the C-arm 16 with the device 12 in the unlocked and locked configurations, respectively. The end (e.g., end 76, 88) is as described above in FIG. 4. The depicted portion 92 coupled to the end structure 90 is retractable. As depicted, the portion 92 includes a ball 122 (e.g., bearing) and a spring 124 (e.g., weak spring) that enables the ball 122 to retract towards (e.g., within) the surface 110 of the end structure 90 in the presence of sufficient force on the ball 122 (e.g., in the locked configuration) to enable the pad 112 to contact an inner surface 126 of the track 14 (see FIG. 6). In the absence of sufficient force on the portions 92 (e.g., in the unlocked configuration), the ball 122 extends away from the surface 110 of the end structure 90 to keep the pad 112 from sufficiently contacting and gripping the inner surface 126 of the track 14 (e.g., to generate enough friction) to block movement of the device 12. In certain embodiments, the retractable portions 92 may include protrusions, feet, spring plungers, or another weak spring loaded device.

Figure 7:
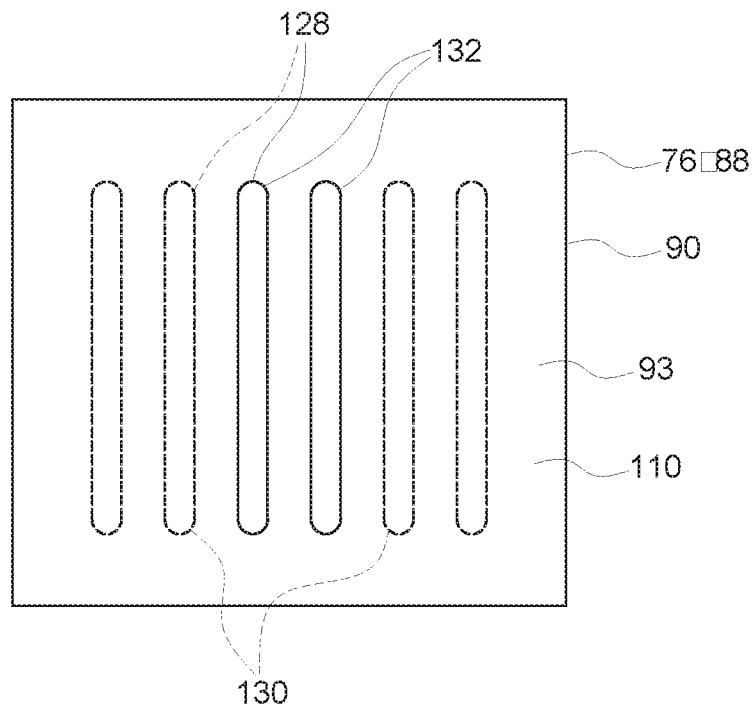
FIG. 7 is an end view of an embodiment of a surface (e.g., having ridges) of an end structure of an end of the orbital rotation positioning device of FIG. 2.
Figure 8:
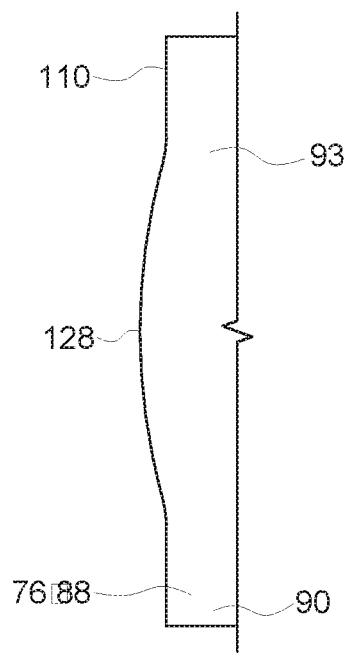
FIG. 8 is a side view of an embodiment of a portion of the surface of FIG. 7.

In certain embodiments, the ends 76, 88 may not include the pad 112 but instead the surface 110 of the end structure 90 may directly interface with the inner surface 126 of the track 14 (e.g., via ridges or protrusions). FIGS. 7 and 8 are an end view and side view, respectively, of an embodiment of the surface 110 of the end structure 90 of an end (e.g., end 76, 88) of the orbital rotation positioning device 12 of FIG. 2. As depicted, the surface 110 of the end structure 90 may include a plurality of ridges or protrusions 128 extending away from the surface 110 (e.g., axially along the longitudinal length 48). In the locked configuration, a sufficient number of ridges 128 (e.g., both the ridges 130 in dashed lines and the ridges 132 in solid lines in FIG. 7) on the surface 110 of the end structure 90 may contact and grip the surface of the track 14 to create enough friction to block movement of the device 12 along the track 14. In the unlocked configuration, only a few ridges (e.g., only ridges 132 in FIG. 7) on the surface 110 of the end structure 90 may contact the surface of the track 12, thus, not creating enough friction to block movement of the device 12.

Figure 9:
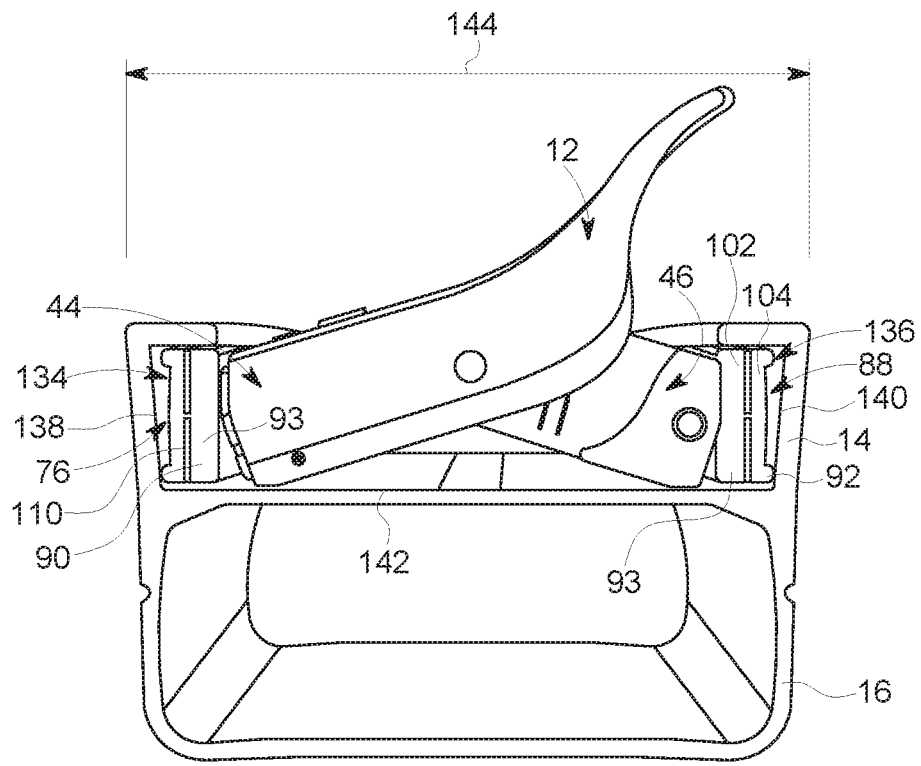
FIG. 9 is a side view of an embodiment of the orbital rotation positioning device of FIG. 2 in an unlocked configuration disposed within a track of a C-arm.
Figure 10:
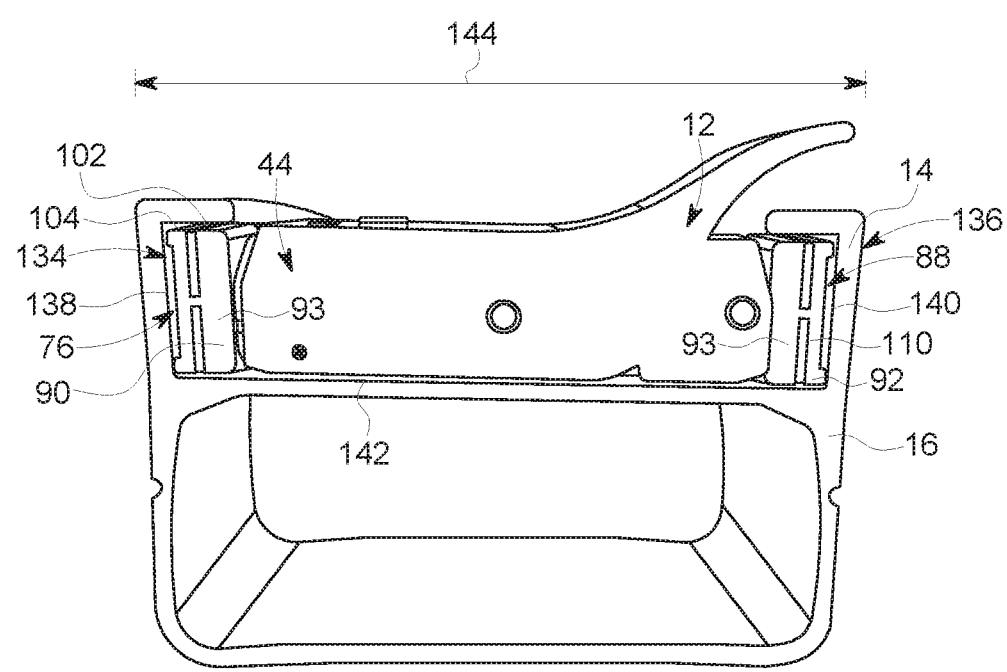
FIG. 10 is a side view of an embodiment of the orbital rotation positioning device of FIG. 2 in a locked configuration disposed within a track of a C-arm.

FIGS. 9 and 10 are side views of an embodiment of the orbital rotation positioning device 12 of FIG. 2 in unlocked and locked configurations, respectively, disposed within the track 14 of the C-arm 16. The device 12 is as described in FIG. 2 above. As depicted, the track 14 includes opposing ends 134, 136 (e.g., having a C-shape) having inner surfaces 138, 140, respectively, and an inner surface 142 extending between the opposing ends 134, 136. As depicted, the device 12 extends across an entire width 144 (e.g., between the inner surfaces 138, 140) of the track 14. Also, the ends 76, 88 of the device 14 interface with the inner surfaces 138, 140 of the track 14, respectively. In FIG. 9, in the unlocked configuration, the portions 92 extend sufficiently away from the ends 76, 88 and the end structure 90 to keep the surface 110 and/or the pad 112 (not shown) between the portions 92 from either contacting and/or sufficiently gripping the surface of the track 14 to enable the device 12 to be slid along the track 14 (e.g., along the surface 142). In the locked configuration, the second layer 104 near the portion 92 is pushed (e.g., axially) towards the first layer 102 to enable the surface 110 and/or the pad 112 between the portions 92 to contact and sufficiently grip the surface of the track 14 (e.g., creates sufficient friction) to block movement of the device 12 along the track 14.

Figure 11:
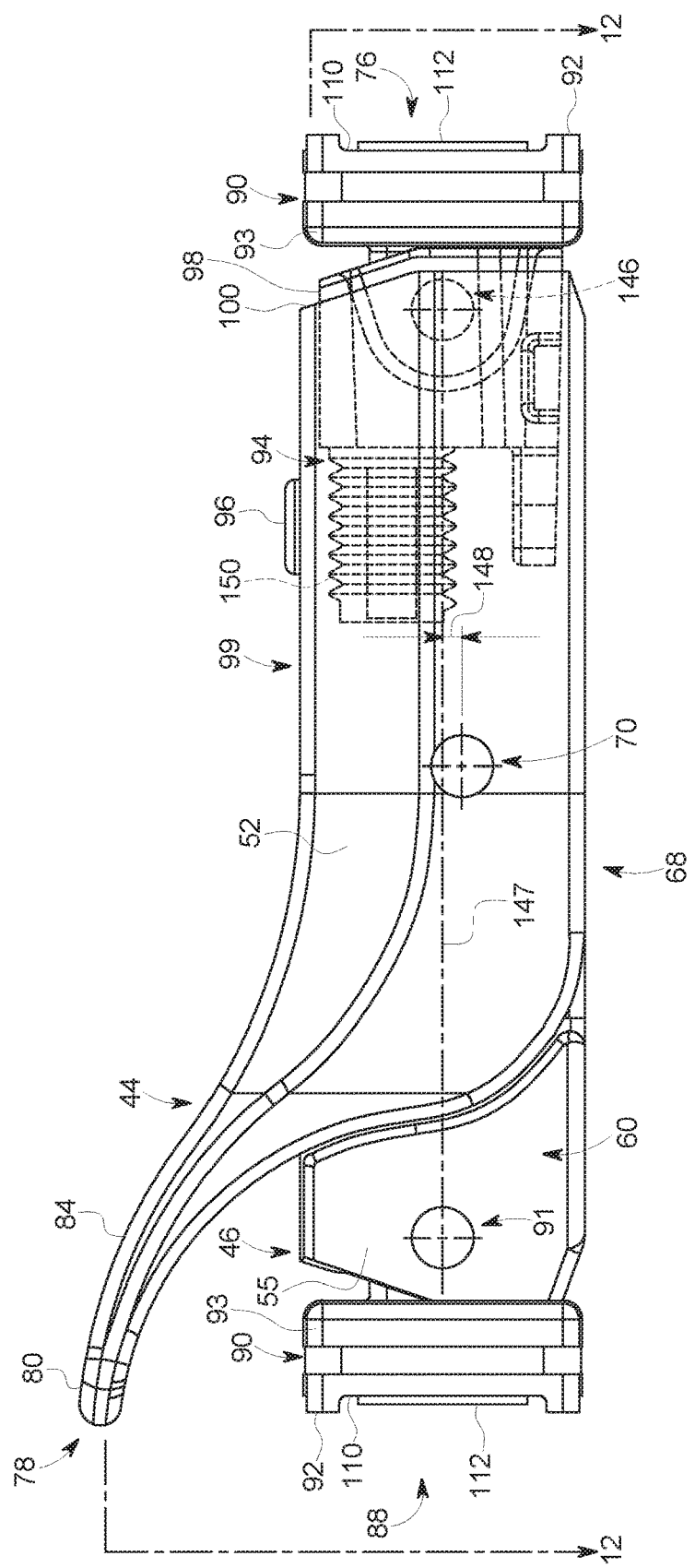
FIG. 11 is a side view of the orbital rotation positioning device of FIG. 2 in a locked configuration.

FIG. 11 is a side view of the orbital rotation positioning device 12 of FIG. 2 in a locked configuration. The orbital rotation positioning device 12 is as described above. As depicted in FIG. 11, the end structure 90 at end 76 is coupled to the first body portion 44 via a fastener 146 (e.g., pin, rivet, etc.). In the locked configuration, the fastener 70 coupling the body portions 44, 46 moves (e.g., radially relative to the longitudinal length 48) below a plane 147 (e.g., goes over center) between the fasteners 91, 146 to create an offset 148. The offset 148 causes the locking action on the device 12.

Figure 12:
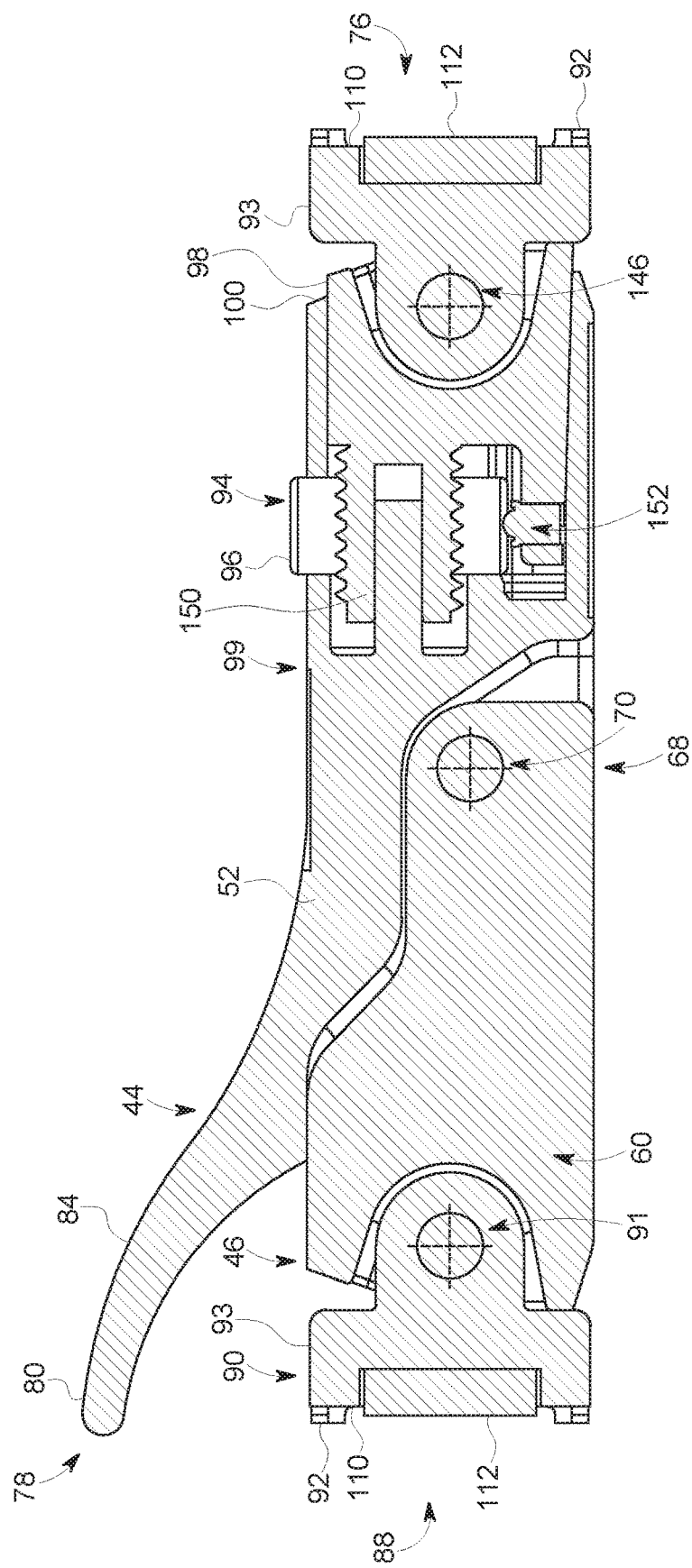
FIG. 12 is a side cross-sectional view of the orbital rotation positioning device of FIG. 11, taken along line 12-12.

Also, depicted in FIGS. 11 and 12 are components of the length adjusting mechanism 94. In particular, a screw 150 is coupled to the telescoping portion or extension 98 disposed between the end structure 90 and the end 100 of the main portion 99 of the first body portion 44. The extension 98 is partially disposed within the main portion 99 of the first body portion 44. Also, the extension 98 couples the end structure 90 to the main portion 99 of the first body portion 44. The knob 96 is disposed about the screw 150. The knob 96 also contacts a ball plunger 152 that interfaces with the grooves on the knob 96. The ball plunger 152 maintains the position of the knob 95 relative to the screw 150 in the absence of turning the knob 96. Rotation of the knob 96 (e.g., circumferentially relative to the longitudinal length 48) in a first circumferential direction causes the extension 98 (and thus the end 76) to extend away (e.g., axially relative to the longitudinal length 48) from the main portion 99 of the first body portion 44 to lengthen the longitudinal length 48 of the device 12. Rotation of the knob in a second circumferential direction (opposite the first circumferential direction) causes the extension 98 (and thus the end 76) to retract (e.g., axially relative to the longitudinal length 48) towards the main portion 99 of the first body portion 44 to shorten the longitudinal length 48 of the device 12.

Figure 13:
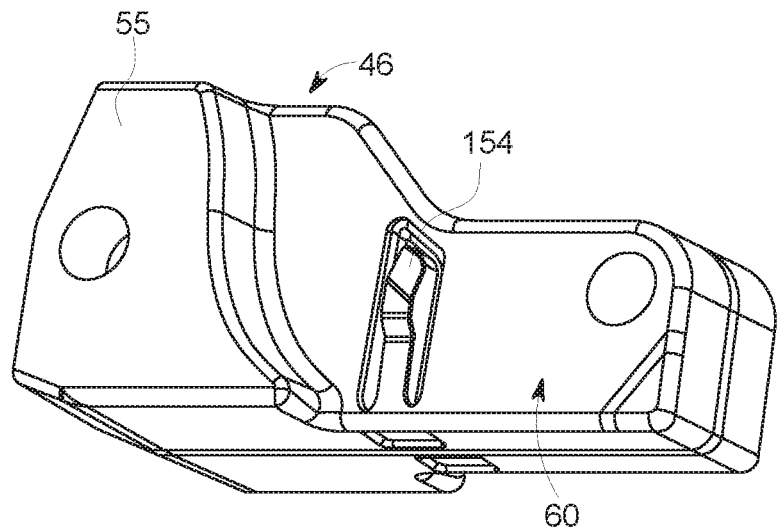
FIG. 13 is a perspective view of a body portion of the orbital rotation positioning device of FIG. 2 having leaf springs.
Figure 14:
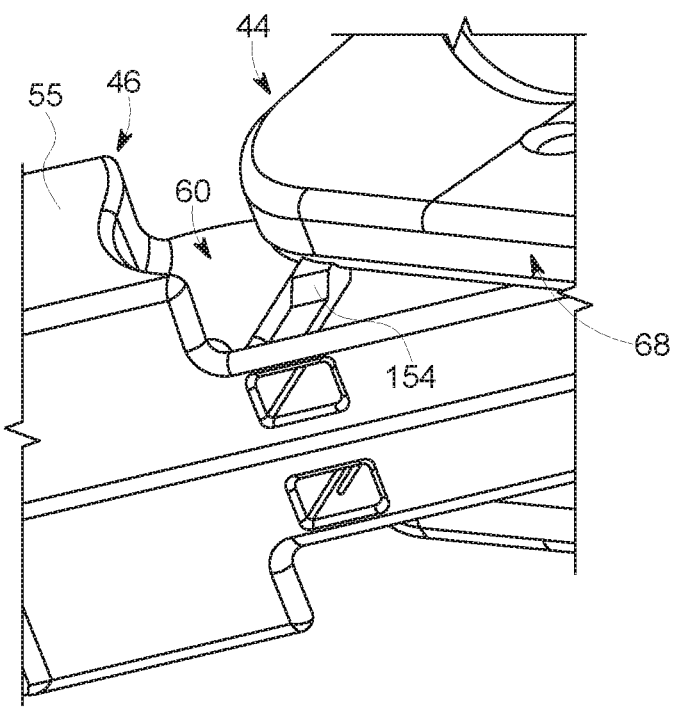
FIG. 14 is a perspective view of a portion of body portions of the orbital positioning device of FIG. 2 in the unlocked configuration.

FIG. 13 is a perspective view of the second body portion 46 of the orbital rotation positioning device 12 of FIG. 2 having leaf springs 154. A leaf spring 154 may be disposed on the opposing sides 58, 60 of the second body portion 46. In the unlocked configuration, portions of the leaf springs 154 extend outward from the respective sides 58, 60. The portions of the leaf springs 154 extending outward keep the device 12 in the unlocked configuration (i.e., keep the first body portion 44 from moving relative to the second body portion 46 into the locked configuration) as depicted in FIG. 14. Pressing the portions of the leaf springs 154 extending outward in enables the first body portion 44 to move relative to the second body portion 46 to put the device 12 in the locked configuration.

Technical effects of the disclosed embodiments include providing a device (e.g., orbital rotation positioning device) to enable a position (e.g., orbital angular position) a C-arm of an X-ray imaging system to be set and returned to quickly and easily. In particular, the device is configured to be disposed within the track and to be set into different configurations. In a first configuration (e.g., locked configuration), the device can be locked into a position along the track (i.e., does not move relative to the track) to block rotation (e.g., in the orbital direction) of the C-arm beyond the position of the device. In a second configuration (e.g., unlocked configuration), the device can be unlocked to enable it to be slid along the track to a different position and/or to be removed from the track. The device is easy to use, intuitive, inexpensive, robust, and adjustable.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An X-ray imaging system, comprising:
   an X-ray radiation source;
   an X-ray detector;
   a C-arm having the X-ray radiation source disposed on a first end and the X-ray detector disposed on a second end opposite the first end, wherein the C-arm comprises a track;
   a C-arm rotation device configured to enable the C-arm to rotate along the track in an orbital direction relative to the C-arm rotation device, wherein a portion of the C-arm rotation device is disposed within the track; and
   an orbital rotation positioning device configured to be disposed within the track, wherein the orbital rotation positioning device blocks rotation of the C-arm beyond a position of the orbital rotation positioning device.

2. The X-ray imaging system of claim 1, wherein the orbital positioning device is configured to block movement of the C-arm upon the portion of the C-arm rotation device contacting the orbital positioning device.

3. The X-ray imaging system of claim 1, wherein the orbital rotation positioning device is configured to interchange between a first configuration and a second configuration, the first configuration is configured to lock the position of the orbital rotation positioning device within the track so that the orbital rotation positioning device does not move relative to the track, and the second configuration is configured to enable the position of the orbital rotation positioning device to be moved along the track.

4. The X-ray imaging system of claim 3, wherein the second configuration is configured to enable the orbital rotation positioning device to be removed from the track.

5. The X-ray imaging system of claim 3, wherein the orbital rotation positioning device comprises a first body portion having a first end configured to interface with a first surface of the track and a second body portion having a second end configured to interface with a second surface of the track opposite the first surface, wherein the first body portion is moveable relative to the second body portion.

6. The X-ray imaging system of claim 5, wherein the first body portion is configured to be rotated about an axis perpendicular to a longitudinal length of the orbital rotation positioning device.

7. The X-ray imaging system of claim 5, wherein the first body portion comprises a handle, and wherein a force applied in the first direction upon the handle sets the orbital rotation positioning device in the first configuration, and the force applied in the second direction upon the handle sets the orbital rotation positioning device in the second configuration.

8. The X-ray imaging system of claim 5, wherein both the first and second ends each comprise an end surface configured both to grip a respective surface of the track when in the first configuration and to not grip the respective surface of the track when in the second configuration.

9. The X-ray imaging system of claim 1, wherein the orbital rotation positioning device is configured to be disposed across an entire width of the track.

10. The X-ray imaging system of claim 1, wherein the orbital rotation positioning device is configured to have a length adjusted via a length adjusting mechanism.

11. The X-ray imaging system of claim 10, wherein the length adjusting mechanism comprises a nut and screw assembly disposed within the orbital rotation positioning device.

12. An orbital rotation positioning device, comprising:
 a first body portion having a first end configured to interface with a first surface of a track of a C-arm of an X-ray imaging system; and
 a second body portion having a second end configured to interface with a second surface of the track opposite the first surface of the C-arm of the X-ray imaging system, wherein the first body portion is moveable relative to the second body portion;
 wherein the orbital rotation positioning device is configured to be disposed within the track of the C-arm to block rotation of the C-arm beyond a position of the orbital rotation positioning device, and wherein the orbital rotation positioning device is configured to interchange between a first configuration and a second configuration, the first configuration is configured to lock the position of the orbital rotation positioning device within the track so that the orbital rotation positioning device does not move relative to the track, and the second configuration is configured to enable the position of the orbital rotation positioning device to be moved along the track.

13. The orbital rotation positioning device of claim 12, wherein both the first and second ends each comprise an end surface configured both to grip a respective surface of the track when in the first configuration and to not grip the respective surface of the track when in the second configuration.

14. The orbital rotation positioning device of claim 13, wherein both the first and second ends each comprise an end structure comprising a plurality of portions that contact the respective surface of the track when in the second configuration to keep the end surface from gripping the respective surface.

15. The orbital rotation positioning device of claim 14, wherein each portion of the plurality of portions comprises a protrusion that extends away from the end structure towards the respective surface.

16. The orbital rotation positioning device of claim 15, wherein each protrusion comprises a mechanism that enables the protrusion to extend away from the end structure towards the respective surface when in the second configuration and to retract towards the end structure away from the respective surface when in the first configuration.

17. The orbital rotation positioning device of claim 12, wherein the first body portion is configured to be rotated about an axis perpendicular to a longitudinal length of the orbital rotation positioning device.

18. The orbital rotation positioning device of claim 12, wherein the first body portion comprises a handle, and wherein a force applied in the first direction upon the handle sets the orbital rotation positioning device in the first configuration, and the force applied in the second direction upon the handle sets the orbital rotation positioning device in the second configuration.

19. The orbital rotation positioning device of claim 12, wherein the orbital rotation positioning device is configured to have a length adjusted via a nut and screw assembly disposed within the orbital rotation positioning device, where the length is adjusted by extending the first end away from the first body portion or retracting the first end towards the first body portion.

20. An orbital rotation positioning device, comprising:
 a first body portion having a first end comprising a first end structure having a first end surface disposed on a flexible surface, and the first end surface is configured to interface with a first surface of a track of a C-arm of an X-ray imaging system; and
 a second body portion having a second end comprising a second end structure having a second end surface, and the second end surface is configured to interface with a second surface of the track opposite the first surface of the C-arm of the X-ray imaging system, wherein the first body portion is moveable relative to the second body portion;
 wherein the orbital rotation positioning device is configured to be disposed within the track of the C-arm to block rotation of the C-arm beyond a position of the orbital rotation positioning device, and wherein the orbital rotation positioning device is configured to interchange between a first configuration and a second configuration, the first configuration is configured to lock the position of the orbital rotation positioning device within the track so that the orbital rotation positioning device does not move relative to the track by having the first end surface and the second end surface respectively grip the first and second surfaces of the track, and the second configuration is configured to enable the position of the orbital rotation positioning device to be moved along the track by having respective portions of the first and second end structures extend away from the first and second end structures to contact the first and second surfaces, respectively, to keep the first and second end surfaces from gripping the first and second surfaces, respectively.

* * * * *